(12) United States Patent
Yamada et al.

(10) Patent No.: US 8,754,241 B2
(45) Date of Patent: Jun. 17, 2014

(54) ORGANIC COMPOUND AND ELECTROCHROMIC ELEMENT HAVING THE SAME

(71) Applicant: Canon Kabushiki Kaisha, Tokyo (JP)

(72) Inventors: Kenji Yamada, Yokohama (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/745,558

(22) Filed: Jan. 18, 2013

(65) Prior Publication Data
US 2013/0190513 A1    Jul. 25, 2013

(30) Foreign Application Priority Data
Jan. 23, 2012   (JP) .................................. 2012-011300

(51) Int. Cl.
*C07D 495/14* (2006.01)

(52) U.S. Cl.
USPC ........................................................ 549/43

(58) Field of Classification Search
USPC ........................................................ 549/43
See application file for complete search history.

(56) References Cited

U.S. PATENT DOCUMENTS

2012/0314272 A1* 12/2012 Yamada et al. ............... 359/265

FOREIGN PATENT DOCUMENTS

JP      56-67881 A      6/1981

OTHER PUBLICATIONS

Schroth et al., 1,2-Dithiins and Precursors, XVII: Synthesis and Properties of Thieno Anellated 1,2-Dithiins, Structural Influence on Colour, 1997, Tetrahedron, vol. 53, No. 22, 7509-7528.*
Michael G. Hill EtAl., "Oligothiophene Cation Radicals", Chem Matter, 1992, 4, 1106-1113.

* cited by examiner

*Primary Examiner* — Kristin Vajda
(74) *Attorney, Agent, or Firm* — Canon U.S.A., Inc., IP Division

(57) ABSTRACT

An organic compound represented by the following general formula [1] is provided. In the general formula [1], $A_1$ to $A_4$ are each independently selected from the group consisting of a hydrogen atom, an alkyl group having 1 to 20 carbon atoms, an alkoxy group having 1 to 20 carbon atoms, and an aryl group. However, at least one of $A_1$ to $A_4$ represents the alkyl group, the alkoxy group, or the aryl group.

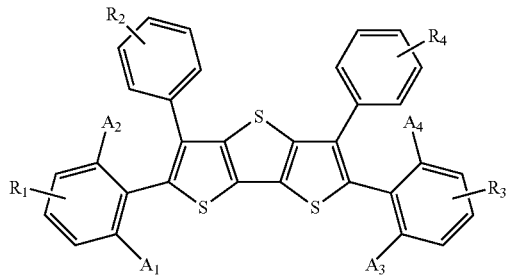

3 Claims, 3 Drawing Sheets

ORGANIC COMPOUND AND ELECTROCHROMIC ELEMENT HAVING THE SAME

BACKGROUND OF THE INVENTION

1. Field of the Invention

The present invention relates to a novel organic compound and an electrochromic element having the same.

2. Description of the Related Art

As electrochromic (hereinafter abbreviated to as "EC" in some cases) materials, the optical absorption properties (colored state, light transmittance, and the like) of which are changed by an electrochemical oxidation-reduction reaction, various materials have been reported. As inorganic EC materials, a compound using a metal oxide, such as $WO_3$, has been known.

As organic EC materials, for example, a conductive polymer used in an EC element described in Japanese Patent Laid-Open No. 56-67881 and an EC material using an organic low molecular weight compound, such as an oligothiophene, disclosed in M. G. Hill, J. F. Penneau, B. Zinger, K. R. Mann, L. L. Miller, Chemistry of Materials, 4 (1992) 1106 have been known.

When the conductive polymer described in Japanese Patent Laid-Open No. 56-67881 is electrochemically oxidized or reduced, the π-conjugated chain length of its main chain is changed, and as a result, the absorption wavelength is changed.

When being in a neutral state, these conductive polymers have absorption in the visible light region and hence are colored, and when the polymers are in an oxidized state, the absorption wavelength shifts to a long wavelength side (infrared region side). That is, the absorption is no longer present in the visible light region, and as a result, the EC element loses its color.

In addition, in the oligothiophene compounds described in Chemistry of Materials, 4 (1992) 1106, it has been disclosed that when an oligothiophene derivative is oxidized or reduced in a solution, the absorption wavelength thereof is changed and that when a terminal group of the oligothiophene derivative is blocked by a substituent group, its oxidative polymerization can be suppressed.

According to Japanese Patent Laid-Open No. 56-67881, unstable radical cations are delocalized in the molecule to enhance the stability thereof. However, the stability is not sufficient, and when oxidation and reduction reactions are repeatedly performed, the material is deteriorated, and as a result, the performance thereof is also disadvantageously degraded.

In addition, when being in a neutral state, this conductive polymer has an absorption band in the visible light region. Hence, at portions at which an electrochemical reaction insufficiently occurs, the colored state still slightly remains, and hence high transparency is difficult to achieve.

In Chemistry of Materials, 4 (1992) 1106, aromatic compounds, such as an oligothiophene compound, having π electrons have been disclosed.

Products formed by oxidation of the disclosed aromatic compounds are in an equilibrium state between radical cation monomers and dimers (π-dimers) generated by their overlapped π electron clouds.

The absorption wavelength of the π-dimer is different from that of the radical cation monomer. Furthermore, the abundance ratio between the π-dimers and the radical cation monomers has the temperature dependence.

Since the light absorption wavelength and the light absorption intensity in the colored state have the temperature dependence, when an EC element is used as a device, the color thereof is disadvantageously changed by the change in temperature.

SUMMARY OF THE INVENTION

The present invention provides an organic compound having excellent stability against oxidation-reduction repetition, high transparency without having light absorption in the visible light region in a bleached state, and excellent color stability against the change in temperature by suppressing π-dimer formation in a colored state.

Accordingly, the present invention provides an organic compound represented by the following general formula [1].

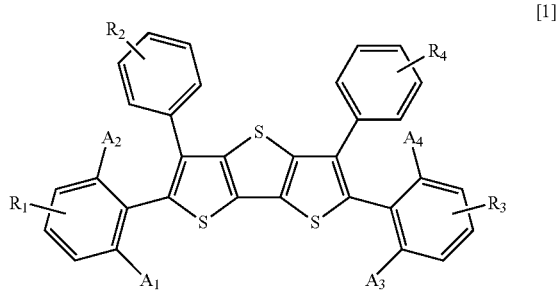

In the general formula [1], $A_1$ to $A_4$ are each independently selected from the group consisting of a hydrogen atom, an alkyl group having 1 to 20 carbon atoms, an alkoxy group having 1 to 20 carbon atoms, and an aryl group. However, at least one of $A_1$ to $A_4$ represents the alkyl group, the alkoxy group, or the aryl group.

The aryl group may have an alkyl group having 1 to 4 carbon atoms or an alkoxy group having 1 to 4 carbon atoms as a substituent.

$R_1$ to $R_4$ each independently represent a hydrogen atom, a halogen atom, an alkyl group having 1 to 20 carbon atoms, an alkoxy group having 1 to 20 carbon atoms, an alkyl ester group having 1 to 20 carbon atoms, an aryl group, or a cyano group.

The aryl group may have an alkyl group having 1 to 4 carbon atoms as a substituent.

Further features of the present invention will become apparent from the following description of exemplary embodiments with reference to the attached drawings.

DESCRIPTION OF THE EMBODIMENTS

An organic compound according to the present invention is represented by the following general formula [1].

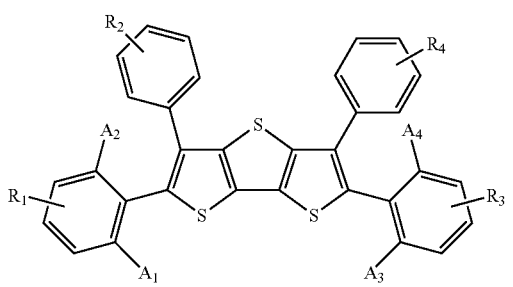

[1]

In the general formula [1], $A_1$ to $A_4$ are each independently selected from the group consisting of a hydrogen atom, an alkyl group having 1 to 20 carbon atoms, an alkoxy group having 1 to 20 carbon atoms, and an aryl group. However, at least one of $A_1$ to $A_4$ represents the alkyl group, the alkoxy group, or the aryl group.

The aryl group may have an alkyl group having 1 to 4 carbon atoms or an alkoxy group having 1 to 4 carbon atoms as a substituent.

$R_1$ to $R_4$ each independently represent a hydrogen atom, a halogen atom, an alkyl group having 1 to 20 carbon atoms, an alkoxy group having 1 to 20 carbon atoms, an alkyl ester group having 1 to 20 carbon atoms, an aryl group, or a cyano group.

The aryl group may have an alkyl group having 1 to 4 carbon atoms as a substituent.

As the alkyl group having 1 to 20 carbon atoms represented by $A_1$ to $A_4$, for example, there may be mentioned a methyl group, an ethyl group, a n-propyl group, an isopropyl group, a n-butyl group, a t-butyl group, a pentyl group, an octyl group, a dodecyl group, a cyclohexyl group, a bicyclooctyl group, and an adamanthyl group.

Furthermore, at least one hydrogen atom of the alkyl group may be substituted by a fluorine atom to form a trifluoromethyl group or the like.

As the alkoxy group having 1 to 20 carbon atoms represented by $A_1$ to $A_4$, for example, there may be mentioned a methoxy group, an ethoxy group, an isopropoxy group, an n-butoxy group, a t-butoxy group, an ethylhexyloxy group, an octyloxy group, and a decyloxy group.

As the aryl group represented by $A_1$ to $A_4$, for example, there may be mentioned a phenyl group, a biphenyl group, a terphenyl group, a fluorenyl group, a naphthyl group, a fluoranthenyl group, an anthryl group, a phenanthryl group, a pyrenyl group, and a perylenyl group.

As the substituent that the aryl group may further has, for example, there may be mentioned a halogen atom, an alkyl group having 1 to 4 carbon atoms, an alkoxy group having 1 to 4 carbon atoms, and an aryl group.

Particular examples of the alkyl group, the alkoxy group, and the aryl group represented by $R_1$ to $R_4$ are similar to the particular examples of the alkyl group, the alkoxy group, and the aryl group, which are the substitutes represented by $A_1$ to $A_4$. In addition, in the alkyl group, at least one hydrogen atom may be substituted by a fluorine atom.

At least one of $A_1$ to $A_4$ represents the alkyl group, the alkoxy group, or the aryl group.

Figure 1:
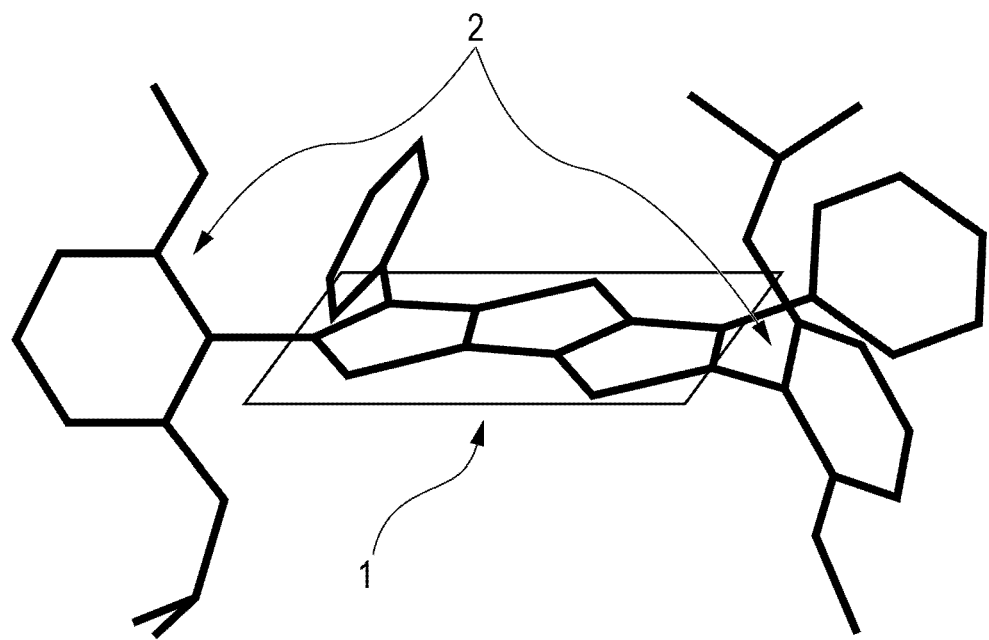
FIG. 1 shows a molecular model of one example of an organic compound according to an embodiment.

FIG. 1 shows a steric structure of one molecule among the organic compounds according to the present invention in which $A_1$ to $A_4$ represent an isopropoxy group or a methoxy group.

Reference numeral 1 indicates a dithienothiophene skeleton, and reference numeral 2 indicates a phenyl group with an isopropoxy group and a methoxy group that serves as a cage moiety.

The dithienothiophene skeleton serving as a core moiety has a structure difficult to make intermolecular contact with other molecules due to the presence of the phenyl groups with $A_1$ to $A_4$ each serving as the cage moiety.

In order to obtain the effect of the substituents $A_1$ to $A_4$ to sterically protect the dithienothiophene structure that is the core serving as a light absorption moiety, the substituents $A_1$ to $A_4$ are each preferably a bulky substituent.

In particular, as the substituents $A_1$ to $A_4$, for example, a methyl group, an ethyl group, a propyl group, an isopropyl group, a n-butyl group, an isobutyl group, a sec-butyl group, a t-butyl group, a dodecyl group, a methoxy group, an isopropoxy group, a t-butoxy group, an ethylhexyloxy group, a phenyl group, and a biphenyl group are preferable. The phenyl group and the biphenyl group each may have an alkyl group as a substituent.

That is, an alkyl group having 1 to 4 carbon atoms, an alkoxy group having 1 to 4 carbon atoms, and a substituted or unsubstituted aryl group are preferable.

Since the substituents represented by $A_1$ to $A_4$ can stabilize radical cations generated at the core moiety by increasing the electron density of the dithienothiophene structure serving as the core moiety, electron donating substituents are more preferable.

As a bulky substituent having high electron donating ability, a lower alkoxy group, such as an isopropoxy group, a t-butoxy group, or an ethylhexyloxy group, is particularly preferable.

When at least one of the group containing $A_1$ and $A_3$ and the group containing $A_2$ and $A_4$ includes an alkyl group, an alkoxy group, or an aryl group, the other group may include a hydrogen atom.

As the substituents represented by $R_1$ to $R_4$, the alkyl group, the alkoxy group, and the aryl group are similar to particular examples of the above alkyl group, alkoxy group, and aryl group, which are represented by $A_1$ to $A_4$.

As the alkyl ester groups represented by $R_1$ to $R_4$, for example, there may be mentioned a methyl ester group, an ethyl ester group, a n-propyl ester group, an isopropyl ester group, a n-butyl ester group, a t-butyl ester group, a pentyl ester group, an isopentyl ester group, a t-amyl ester group, a hexyl ester group, a heptyl ester group, an octyl ester group, an ethylhexyl ester group, a cyclopentyl ester group, and a cyclohexyl ester group.

Among the substituents represented by $R_1$ to $R_4$, an electron donating substituent has an effect of increasing the electron density of the dithienothiophene moiety serving as the core.

Since the oxidation potential is decreased by electron donation of the substituents represented by $R_1$ to $R_4$, an effect of decreasing a driving voltage of an EC element and an effect of enhancing the stability of radical cations generated by oxidation can be obtained.

Hence, as the substituents represented by $R_1$ to $R_4$, a lower alkyl group and a lower alkoxy group, such as a methyl group, an isopropyl group, a methoxy group, and an isopropoxy group, are particularly preferable. The reason for this is that these substituents have high electron donating ability.

Among the substituents represented by $R_1$ to $R_4$, since a polar substituent, such as an alkoxy group or an alkyl ester group, can increase the solubility into a polar solvent, the polar substituent can be preferably used for an EC element in which an electrochromic layer and an electrolytic layer are each formed as a solution layer.

The reason for this is that when an EC material is dissolved at a high concentration in the EC layer and the electrolytic layer, a higher contrast can be obtained in the colored state.

From this point of view, as the substituents represented by $R_1$ to $R_4$, in particular, a methyl ester group, an isopropyl ester group, a t-butyl ester group, a methoxy group, and an isopropoxy group are preferable.

The polar group, such as an alkyl ester, is preferably provided at the meta-position or the para-position of the phenyl group to be linked to dithienothiophene.

The reason for this is to suppress a side reaction between radical cations of dithienothiophene generated by oxidation and a polar group, such as an ester, and a side reaction, such as electropolymerization, accompanied by oxidation-reduction.

That is, when the substituent $R_2$ is introduced in the molecule, in the structure represented by the following general formula [2], at least one of $R_{21}$, $R_{22}$, and $R_{23}$ preferably represents a halogen atom, an alkyl group, an alkoxy group, an alkyl ester group, an aryl group, or a cyano group.

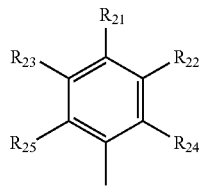

[2]

In the above formula [2], $R_{24}$ and $R_{25}$ each represent a hydrogen atom.

The substituent represented by $R_4$ is also similar to that represented by the general formula [2].

The organic compound according to the present invention has the dithienothiophene structure that is the core serving as a light absorption moiety, phenyl groups having substituents at the ortho-positions introduced at the 2-position and the 6-position of dithienothiophene, and phenyl groups introduced at the 3-position and the 5-position thereof.

The dithienothiophene structure serving as the core of the organic compound according to the present invention is a light absorption moiety.

This dithienothiophene structure is formed by three fused thiophene rings. The π-conjugation system of dithienothiophene is shorter than that of a conductive polymer.

The shorter π-conjugation system indicates high energy of absorption light, and light having high energy has a short wavelength.

Since the organic compound according to the present invention in a neutral state has light absorption in the ultraviolet region and no absorption in the visible light region, high transparency can be obtained. In addition, since having light absorption in the visible light region, the organic compound according to the present invention in the oxidized state is colored.

In the organic compound according to the present invention, even if an electrochemical reaction partially insufficiently occurs, no absorption band is present in the visible light region in the state before oxidation, and hence high transparency can be maintained.

On the other hand, since the conductive polymer has light absorption in the visible light region in the state before oxidation, even in the oxidized state, the colored state slightly may remain in some cases at portions at which the electrochemical reaction insufficiently occurs due to the absorption band present in the visible light region.

Dithienothiophene serving as the core moiety of the compound according to the present invention has a high molecular planarity.

Hence, by the resonance structure, the effect of stabilizing radical cations generated in the oxidized state can be enhanced; however, the stability of radical cations of dithienothiophene is not enough.

Hence, in the compound according to the present invention, the phenyl groups each having substituents at the ortho-positions are introduced at the 2-position and the 6-position of dithienothiophene.

Since the bulky phenyl groups having substituents are introduced, an effect of protecting the dithienothiophene skeleton which generates radical cations can be obtained by the steric hindrance.

Unstableness of radical cations is caused, for example, by recombination between radicals having high reactivity and/or hydrogen abstraction from other molecules by the radicals. That is, the reaction among radicals and other molecules initiated by contact therebetween degrades the stability of radical cations.

Hence, the steric hindrance effect by the phenyl groups having substituents at the ortho-positions to be linked to dithienothiophene can significantly enhance the stability of radical cations. The reason for this is that the steric hindrance group suppresses radical cations from being in contact with other molecules.

For example, when the dithienothiophene skeleton is regarded as the plane, the phenyl groups each having substituents at the ortho-positions are present on the planes nearly perpendicular to the plane of dithienothiophene.

Accordingly, since the bulky phenyl groups each having substituents at the ortho-positions serve as steric hindrance groups, the dithienothiophene skeleton has an effect of suppressing radical cations from being in contact with other molecules (cage effect).

Since suppressing the dithienothiophene moiety (core moiety) from being in contact with other molecules and the like, the structure of the moieties (cage moieties) of the phenyl groups having the steric hindrance groups $A_1$ to $A_4$ more preferably has a molecular shape so as to wrap the core moiety.

Hence, the substituent to be introduced into the phenyl group is preferably bulky.

An electron resonance effect is preferably small between the core moiety and the cage moieties. That is, the resonance structure is preferably not formed between the core moiety and the cage moieties.

Hence, the angle formed between the plane of the core moiety and that of the cage moiety is preferably close to 90°.

From this point of view, a phenyl group having two substituents at two ortho-positions, which is the cage moiety, is preferable as compared to a phenyl group having one substituent at one ortho-position.

As a result, the HOMO (highest occupied molecular orbital) locally present at the core moiety can be suppressed from bleeding into the cage moiety.

In actual molecules, the molecular orbital cannot be completely interrupted due to the presence of quantum chemical fluctuation; however, when the orbital of π electrons of the cage moiety is perpendicular to that of the core moiety, the resonance therebetween cannot been obtained.

Hence, the phenyl group, which is the cage moiety to be linked to the core moiety, preferably has an angle close to 90° with respect to the molecular plane of the core moiety.

In the cage effect of the compound according to the present invention, with respect to a core moiety having a low oxidation potential, a cage moiety having an oxidation potential higher than that of the core moiety is preferably provided.

A moiety having a high oxidation potential is stable against oxidation.

Since being localized at the core moiety in the structure described above, radicals and cations in the oxidized state are not likely to be brought into contact with other molecules and the like present outside, and hence the stability of radical cations can be significantly improved.

By the presence of the phenyl groups located at the 3-position and the 5-position of dithienothiophene serving as the core moiety, the compound according to the present invention has three types of effects.

As a first effect, the cage effect by the moieties (cage moieties) of the phenyl groups having the steric hindrance groups $A_1$ to $A_4$ can be further enhanced.

Since dithienothiophene is substituted by the phenyl groups at the 3-position and the 5-position, the planes of the phenyl groups introduced at the 2-position and the 6-position of dithienothiophene are each likely to have a molecular structure having an angle close to 90° with respect to the plane of dithienothiophene.

The reason for this is that because of the steric hindrance caused by the phenyl groups located at the 3-position and the 5-position of dithienothiophene, the steric hindrance groups $A_1$ to $A_4$ can be stabilized in terms of energy when being located at an angle close to 90° with respect to the plane of dithienothiophene.

As a second effect, since being substituted by the phenyl groups, hydrogen atoms located at the 3-position and the 5-position of dithienothiophene, which may react with radical cations, are removed, and as a result, the stability can be enhanced.

As a third effect, since the contact with other molecules is suppressed, an effect of suppressing the formation of dimers (π-dimers) of radical cations generated by oxidation can also be obtained.

It has been known that the π-dimers are generated by overlapping π electron clouds of radical cation monomers.

In the organic compound according to the present invention, the dithienothiophene moiety is isolated by increasing the distance between dithienothiophene molecules with the cage moieties, and as a result, the π electron clouds can be suppressed from being overlapped with each other.

In the organic compound according to the present invention, the formation of π-dimers is suppressed, and hence the abundance ratio of the monomers is high.

Hence, in the oxidized state, coloration caused by the absorption of radical cation monomers occurs.

Since suppressing the formation of π-dimers, the organic compound according to the present invention can suppress the change in electrochromic characteristics (color characteristics) caused by the change in temperature.

When an EC element is used as a device required to have monochromaticity, the suppression of π-dimer formation has a significant effect of improving the monochromaticity of the absorption spectrum.

Hereinafter, examples of particular structural formulas of the compounds according to the present invention will be described. However, the compounds according to the present invention are not limited thereto.

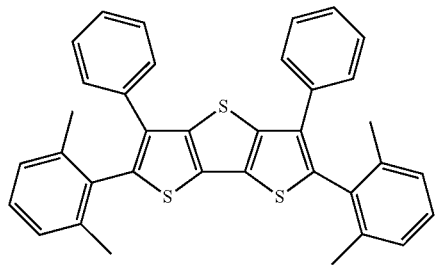

A-1

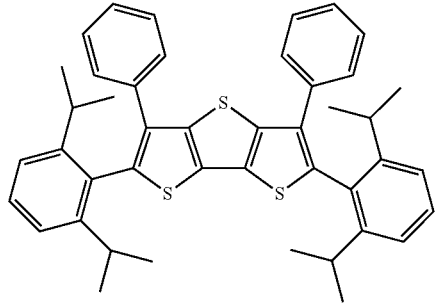

A-2

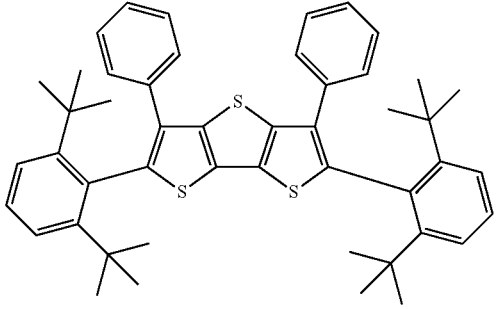

A-3

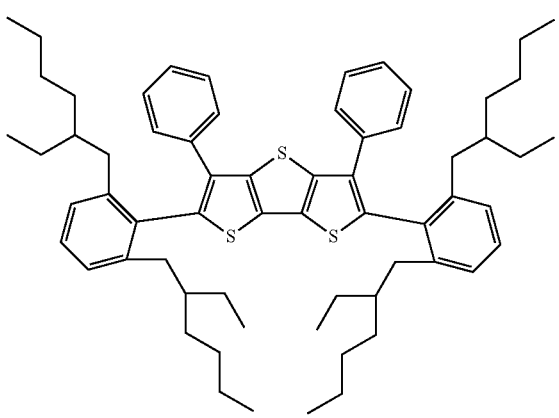

A-4

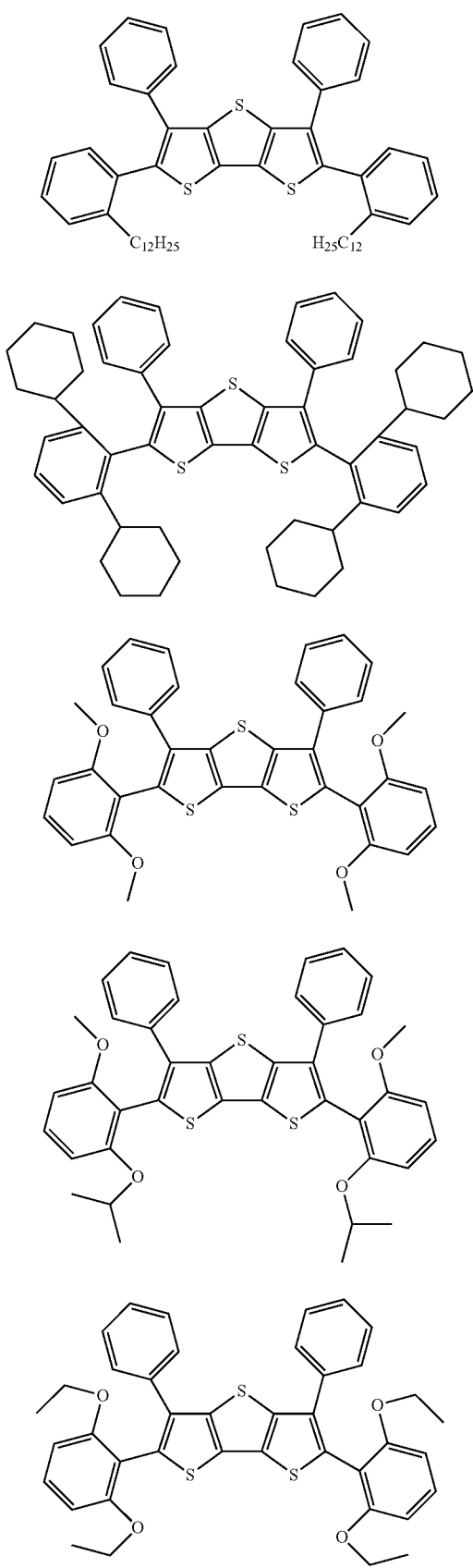
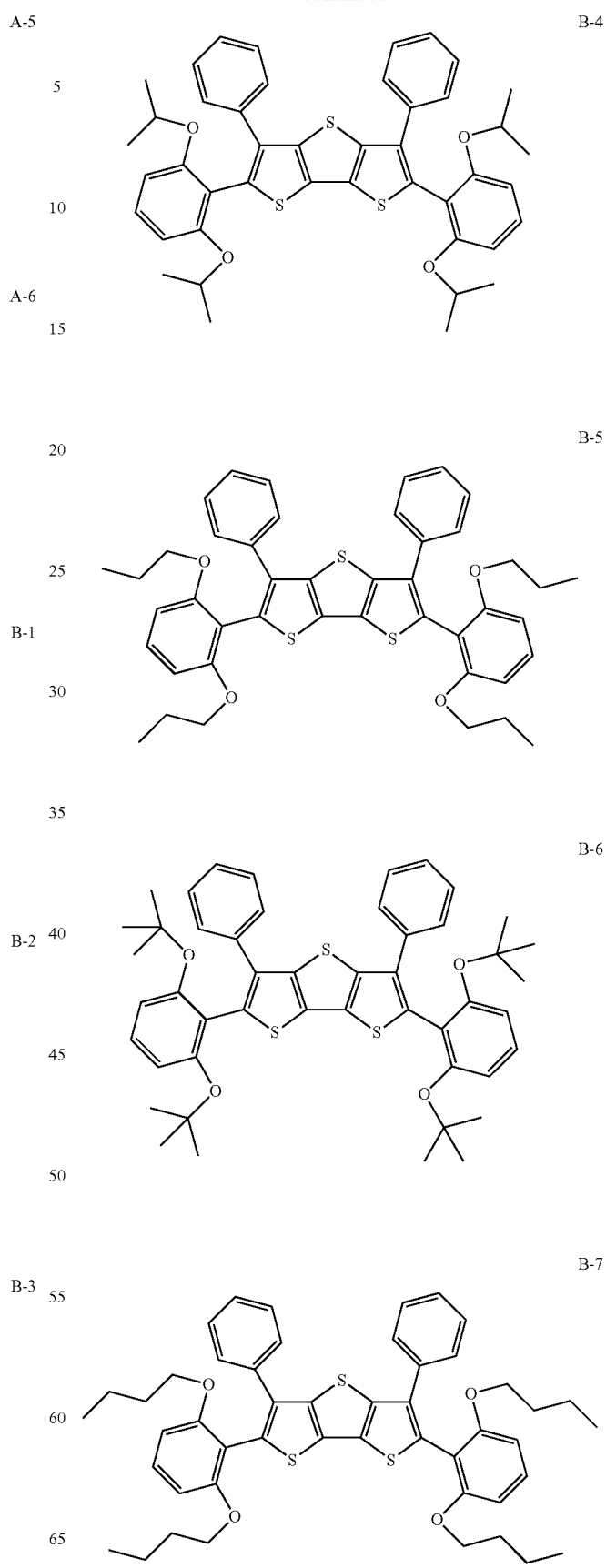

B-8
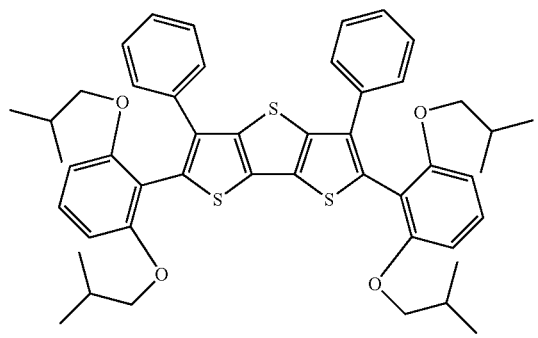
B-9
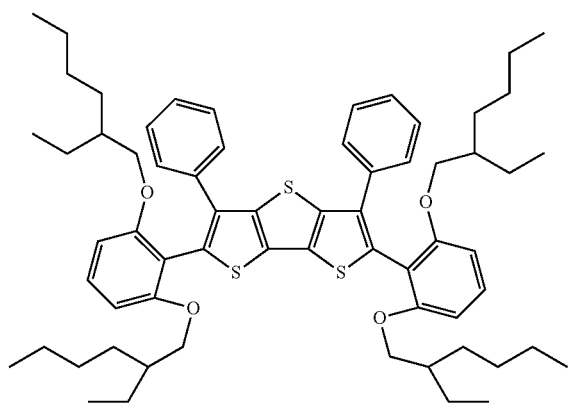
B-10
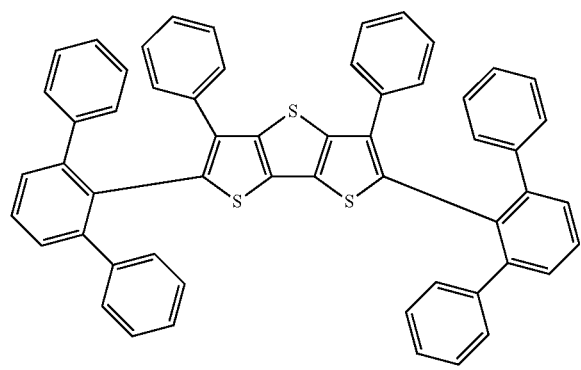
C-2
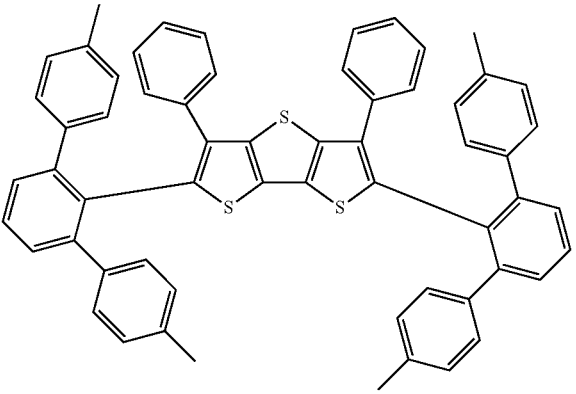
C-3
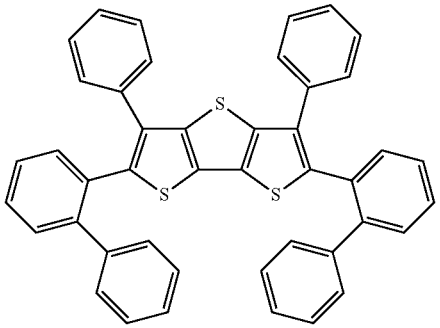
C-4
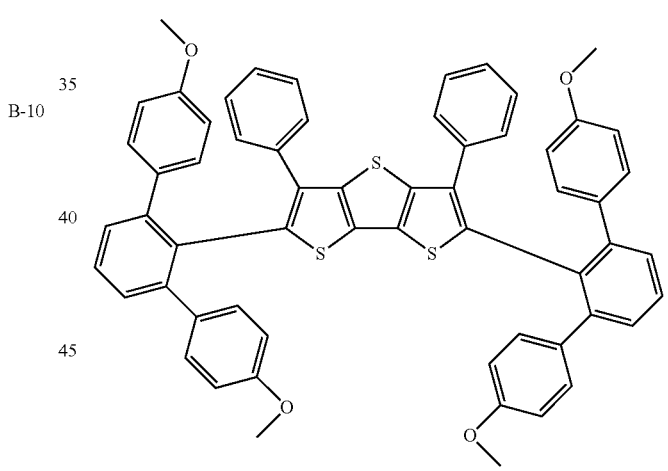
C-1
C-5
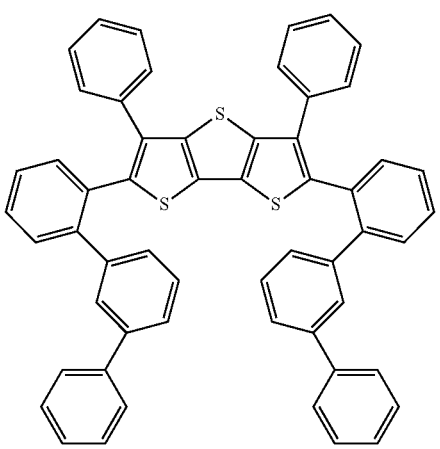

C-6
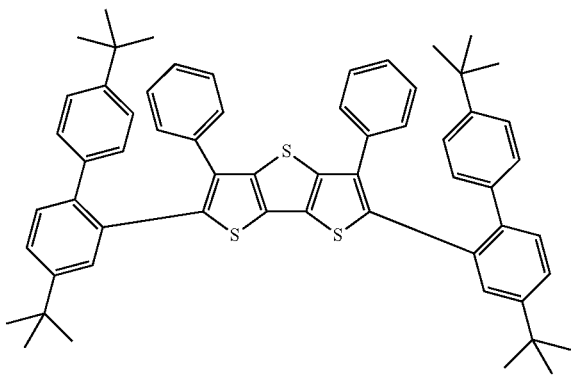
D-1
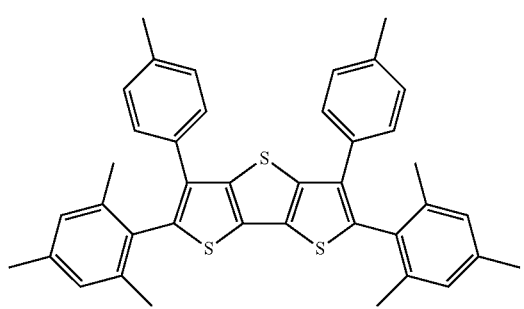
D-2
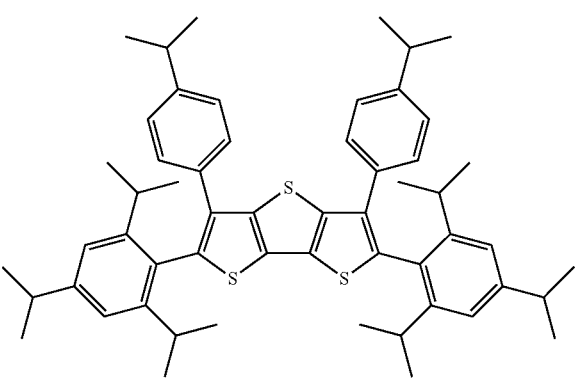
D-3
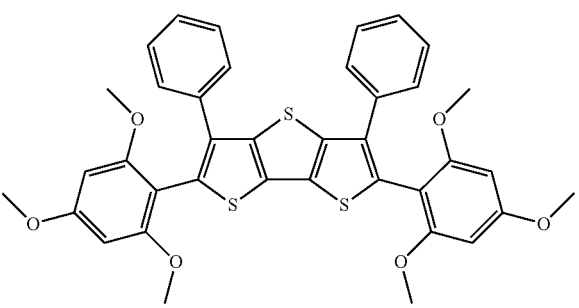
D-4
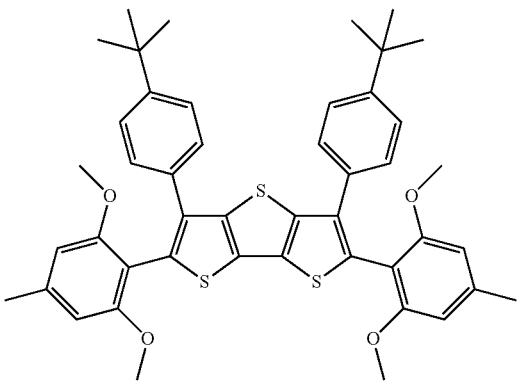
D-5
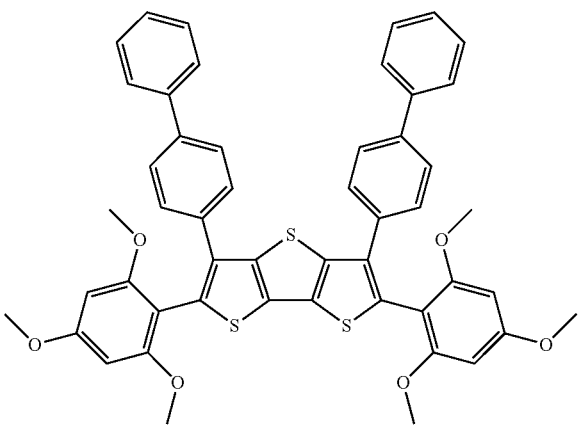
D-6
D-7
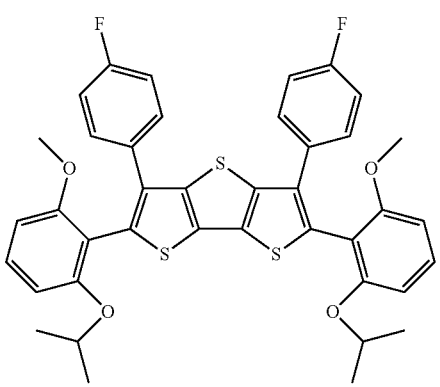

D-8
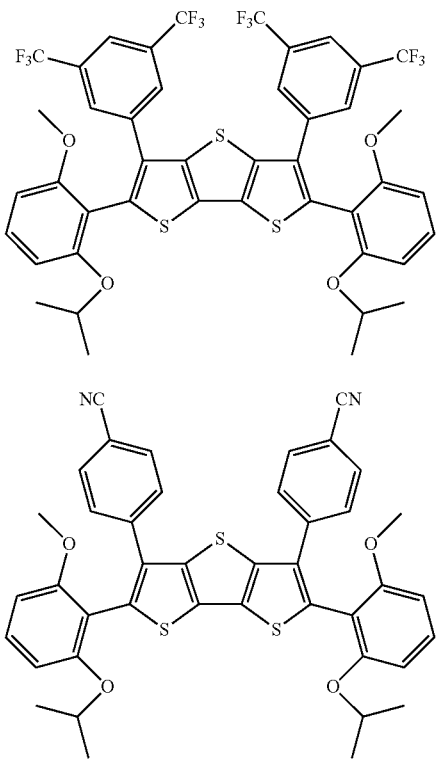

D-9

D-10
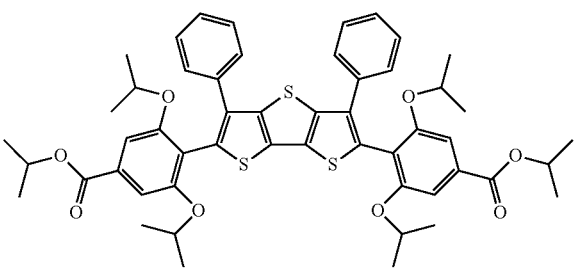

D-11
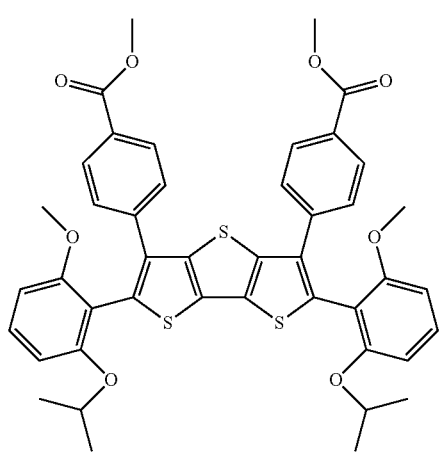

D-12
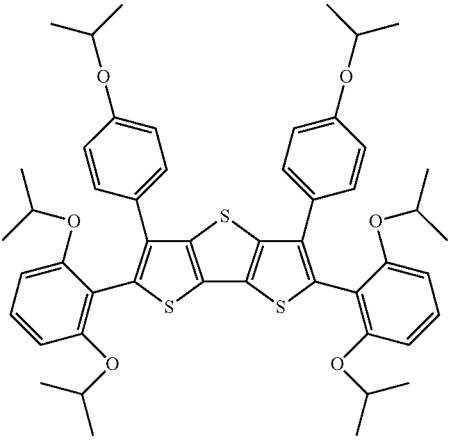

Among the exemplary compounds, in the compounds shown in Group A, $A_1$ to $A_4$ of the general formula [1] each represent an alkyl group or a hydrogen atom; in the compounds shown in Group B, $A_1$ to $A_4$ each represent an alkoxy group or a hydrogen atom; and in the compounds shown in Group C, $A_1$ to $A_4$ each represent an aryl group or a hydrogen atom.

On the other hand, the compounds shown in Group D are compounds in which the groups represented by $R_1$ to $R_4$ of the general formula [1] are partially substituted by a halogen atom, an alkyl group, an alkoxy group, an aryl group, or a cyano group other than a hydrogen atom.

Since being present at the ortho-positions of the substituted phenyl groups, the structures shown by $A_1$ to $A_4$ protect the dithienothiophene structure serving as the core by the cage effect using the steric hindrance.

Hence, EC elements using the compounds mentioned above as EC materials have high durability against oxidation-reduction repetition and are also excellent in color characteristic stability in the colored state against the change in temperature by suppressing the formation of π-dimers.

The organic compound according to the present invention can be synthesized by a reaction represented by the following formula [3]. In the formula, X represents a halogen atom. By a coupling reaction between a halogenated compound, 3,5-dibromothienothiophene, and a phenylboronic acid or a phenyl boronic ester compound, each having a substituent $R_2$, with a Pd catalyst, phenyl groups are introduced at the 3-position and 5-position of dithienothiophene, and after the 2-position and the 6-position thereof are further halogenated, a coupling reaction with a boronic acid or a boronic ester compound, each including a phenyl group having substituents represented by $A_1$ and $A_2$ at the ortho-positions, is performed, so that the organic compound according to the present invention can be obtained. In addition, in the coupling reaction described above, the combination between the halogenated compound and the boronic acid-containing compound may be changed to a reversed combination (boronic acid derivative of dithienothiophene+halogenated compound-containing phenyl group).

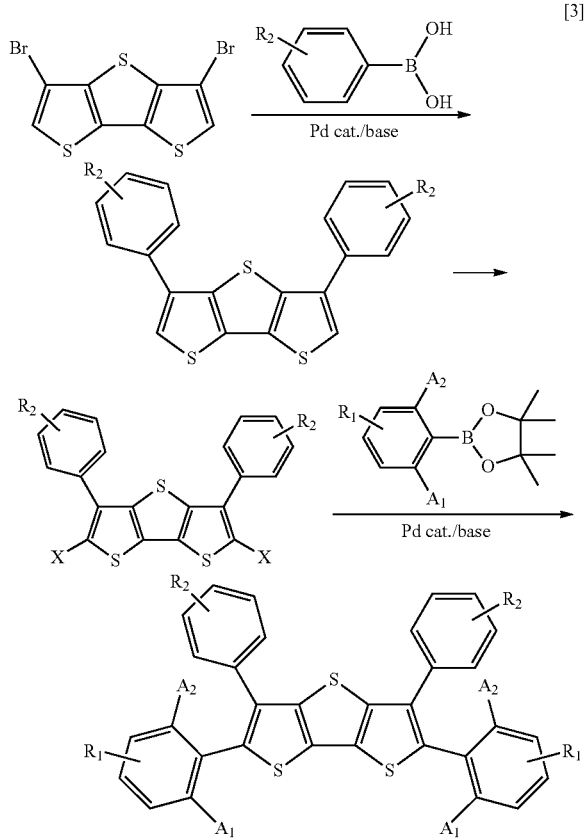

[3]

Next, an EC element of this embodiment will be described.

A first aspect of the EC element of this embodiment is an element including a pair of electrodes and an electrochromic layer and an electrolytic layer arranged between the pair of electrodes. This EC layer contains the organic compound according to the present invention.

The EC element of this embodiment can be obtained by forming a film on an electrode substrate from the organic compound according to the present invention.

The film forming method is not particularly limited, and the film may be formed, for example, by a coating method, such as spin coating, dipping, a casting method, an LB method, or an ink jet method, a vacuum deposition method, an ionized deposition method, sputtering, or a plasma deposition method.

As solvents of coating methods each using a solution, any solvents may be used as long as they can dissolve EC compounds and can be removed after coating by evaporation or the like.

For example, there may be mentioned dimethyl sulfoxide, dimethylacetamide, dimethylformamide, N-methylpyrrolidone, propylene glycol methyl ether acetate, dimethoxyethane, acetonitrile, propionitrile, tetrahydrofuran, dioxane, methanol, ethanol, propanol, chloroform, toluene, xylene, methyl ethyl ketone, and cyclohexanone.

As an ion conductive material used for the electrolytic layer, any salts may be used as long as they are ion-dissociative salts, have excellent solubility into solutions or high compatibility with solid electrolytes, and contains anions having electron donating ability so as to ensure coloration of the EC compound.

For example, a liquid type ion conductive material, a gelled liquid type ion conductive material, or a solid type ion conductive material may be used.

As the liquid type ion conductive material, for example, materials including solvents and supporting electrolytes, such as salts, acids, or alkalis, dissolved therein may be used. As the solvents, any solvents may be used as long as they can dissolve the supporting electrolytes, and in particular, polar solvents are preferable.

In particular, for example, there may be mentioned water and organic solvents, such as methanol, ethanol, propylene carbonate, ethylene carbonate, dimethyl sulfoxide, dimethoxyethane, acetonitrile, γ-butyrolactone, γ-valerolactone, sulfolane, dimethylformamide, dimethoxyethane, tetrahydrofuran, acetonitrile, propionitrile, dimethylacetamide, methylpyrrolidinone, and dioxolane.

As the salts used for the supporting electrolytes, for example, inorganic ionic salts, such as various alkali metal salts and alkaline earth metal salts, quaternary ammonium salts, and cyclic quaternary ammonium salts may be mentioned.

In particular, for example, there may be mentioned alkali metal salts of Li, Na, and K, such as $LiClO_4$, LiSCN, $LiBF_4$, $LiAsF_6$, $LiCF_3SO_3$, $LiPF_6$, LiI, NaI, NaSCN, $NaClO_4$, $NaBF_4$, $NaAsF_6$, KSCN, and KCl; and quaternary ammonium salts and cyclic quaternary ammonium salts, such as $(CH_3)_4NBF_4$, $(C_2H_5)_4NBF_4$, $(n-C_4H_9)_4NBF_4$, $(C_2H_5)_4NBr$, $(C_2H_5)_4NClO_4$, and $(n-C_4H_9)_4NClO_4$.

As the gelled liquid type ion conductive material, highly viscous or gelled materials prepared by further adding a polymer or a gelation agent to the above liquid type ion conductive materials may be used.

As the polymer (gelation agent), for example, there may be mentioned a polyacrylonitrile, a carboxymethylcellulose, a poly(vinyl chloride), a poly(ethylene oxide), a poly(propylene oxide), a polyurethane, a polyacrylate, a polymethacrylate, a polyamide, a polyacrylamide, a polyester, and Nafion (registered trademark).

As the solid type ion conductive material, any materials may be used as long as they are a solid at room temperature and also have ion conductivity, and for example, there may be mentioned a poly(ethylene oxide), a poly(oxyethylene methacrylate), Nafion (registered trademark), and a poly(styrene sulfonate).

These electrolytic materials may be used alone, or at least two of them may be used in combination.

As electrode materials, for example, there may be mentioned metals and metal oxides, such as an indium tin oxide (ITO) alloy, tin oxide (NESA), indium zinc oxide (IZO), silver oxide, vanadium oxide, molybdenum oxide, gold, silver, platinum, copper, indium, and chromium; silicon materials, such as polysilicon and amorphous silicon; and carbon materials, such as carbon black, graphite, and glassy carbon.

In addition, electrically conductive polymers (such as a polyaniline, a polypyrrole, a polythiophene, a polyacetylene, a polyparaphenylene, and a complex between a poly(ethylene dioxythiophene) (PEDOT) and a poly(styrene sulfonate)) having conductivity improved by a doping treatment or the like may also be preferably used.

The EC element of this embodiment can be used for an optical filter. As the optical filter, for example, an ND (neutral-density) filter and a filter for modulating wavelengths may be mentioned.

An optical filter having the EC element of this embodiment may be used for an image pickup element such as a camera. In this case, the position at which the optical filter is installed is not particularly limited. In particular, the optical filter may be installed in front of the image pickup element, may be integrated with an image pickup optical system, such as lenses, or may be installed between the image pickup optical system and the image pickup element.

The drive of the optical filter is controlled by a switching element, such as a TFT element. This switching element is connected to the EC element for the control thereof.

When the optical filter is installed in front of the image pickup element, an image pickup apparatus may include the optical filter.

When the optical filter is integrated with the image pickup optical system, a lens unit including the optical filter may be formed.

Since the optical filter is also required to have transparency, materials having no light absorption in the visible light region, such as ITO, IZO, NESA, and electrically conductive polymers with improved conductivity, are particularly preferably used as the electrode.

Those materials mentioned above may be used in various forms, such as a bulky form and a fine particle form. In addition, those electrode materials may be used alone, or at least two of them may be used in combination.

A method for forming the EC element of this embodiment is not particularly limited, and for example, there may be various methods, such as a method including the steps of forming an EC layer on an electrode substrate and injecting an ion conductive material in a gap provided between the substrate and a sealed counter-electrode substrate by vacuum injection method, an air injection method, a meniscus method, or the like; a method including the steps of forming a layer of an ion conductive material on an electrode substrate or an electrode substrate on which an EC layer is formed and then providing a counter-electrode substrate on the layer; and a method including the step of providing an ion conductive material in the form of a film on a counter-electrode substrate.

A second aspect of the EC element of this embodiment is an element including a pair of electrodes and an electrochromic layer and an electrolytic layer, those layers forming a solution layer, arranged between the pair of electrodes.

The solution layer in this case is not particularly limited as long as it can dissolve the supporting electrolyte as well as the electrochromic material, and a solution layer having a polarity (high dielectric constant) is preferable.

In particular, for example, there may be mentioned water and organic polar solvents, such as methanol, ethanol, propylene carbonate, ethylene carbonate, dimethyl sulfoxide, dimethoxyethane, acetonitrile, γ-butyrolactone, γ-valerolactone, sulfolane, dimethylformamide, dimethoxyethane, tetrahydrofuran, acetonitrile, propionitrile, benzonitrile, dimethylacetamide, methylpyrrolidinone, and dioxolane.

Since being excellent in durability, transparency in the bleached state, and temperature stability of absorption wavelength in the colored state, the electrochromic element of this embodiment may be preferably used for the control of the amount of light incident on an image pickup element, such as a camera, and for the control of incident wavelength distribution characteristics.

Since the incident wavelength distribution is controlled, the color temperature conversion in image taking can be advantageously performed. That is, when the EC element is installed in an optical path of an optical system (lens system) communicating with an image pickup element, the amount of light received by the image pickup element or the incident wavelength distribution characteristics can be controlled.

Since high transparency can be obtained when the EC element is in the bleached state, the incident light passes therethrough at a high transmittance. In addition, in the colored state, since the transmittance of the incident light is decreased, the amount of light received by the image pickup element is decreased.

In addition, excellent oxidation-reduction repetition characteristics and a long operating life can be achieved, and the color stability in the colored state against the change in temperature is also excellent; hence, stable optical characteristics can be obtained even in a wide range of temperature.

According to the present invention, there is provided an organic compound that has high stability against oxidation-reduction repetition, high transparency when bleached in the electrical neutral state, and excellent color stability in the colored state against the change in temperature.

EXAMPLES

Example 1

Synthesis of Exemplary Compound B-2

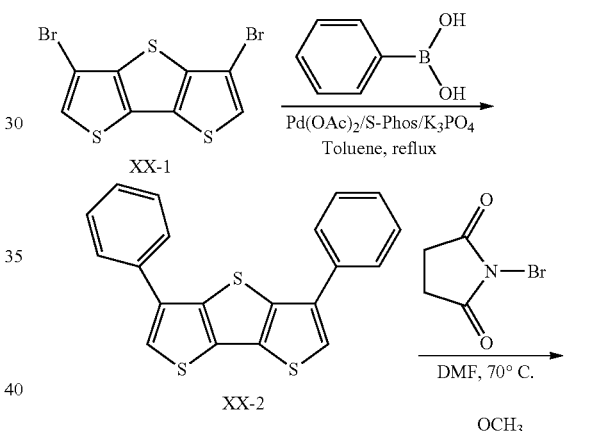

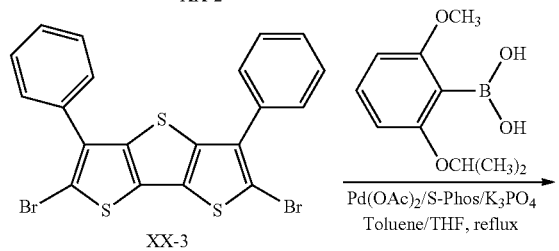

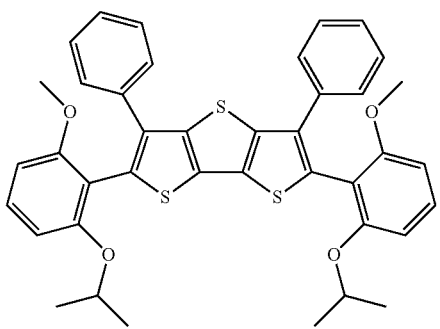

(1) In a 300-mL reaction container, 1.25 g (3.53 mmol) of XX-1 (3,5-dibromodithieno[3,2-b:2',3'-d]thiophene), 1.29 g (10.59 mmol) of phenylboronic acid were dissolved in toluene (70 ml), and dissolved oxygen was removed by nitrogen. Next, 15.9 mg (0.0706 mmol) of Pd(OAc)$_2$, 72.5 mg (0.1765 mmol) of 2-dicyclohexylphosphino-2',6'-dimethoxybiphenyl (S-Phos), and 3.75 g (17.65 mmol) of tripotassium phosphate were added in a nitrogen atmosphere, and a reaction was performed at 140° C. by heat reflux for 13 hours. After a reaction solution was cooled to room temperature, concentration under reduced pressure was performed, and isolation and purification were performed by a silica gel chromatography (moving phase: hexane/ethyl acetate) to give XX-2 as a white solid powder (1.23 g, yield: 100%).

(2) In a 300-mL reaction container, 1.13 g (3.242 mmol) of XX-2 obtained in the above (1) was dissolved in 65 ml of DMF (N,N-dimethylformamide). Next, 1.44 g (8.106 mmol) of N-bromosuccinimide was added, and stirring was performed at 70° C. for 24 hours. After a reaction solution was cooled to room temperature, extraction by chloroform, water washing, and concentration under reduced pressure were performed, and as a result, a pale yellow powder XX-3 was obtained (1.55 g, yield: 94%).

(3) In a 50-ml reaction container, 200 mg (0.395 mmol) of XX-3, 332 mg (1.580 mmol) of 2-isopropoxy-6-methoxyphenylboronic acid were mixed together in a mixed solvent of toluene and tetrahydrofuran (3 ml/3 ml), and dissolved oxygen was removed by nitrogen. Next, 1.8 mg (0.0079 mmol) of Pd(OAc)$_2$, 8.13 mg (0.0198 mmol) of 2-dicyclohexylphosphino-2',6'-dimethoxybiphenyl (S-Phos), and 455 mg (1.98 mmol) of tripotassium phosphate were added in a nitrogen atmosphere, and a reaction was performed by heat reflux for 8 hours. After a reaction solution was cooled to room temperature, concentration under reduced pressure was performed, and isolation and purification were performed by a silica gel chromatography (moving phase: hexane/chloroform=½) to give B-2 as a white solid powder (225 mg, yield: 84%).

By mass analysis (MS) and nuclear magnetic resonance (NMR) measurement, the structure of the compound B-2 was analyzed, and the molecular weight and the ratio of integrated values of NMR peaks well agreed with the structure. In particular, 676 as M$^+$ of this compound was confirmed by a matrix-assisted laser desorption-ionization mass spectrometry (MALDI-MS). In addition, the measurement results of a nuclear magnetic resonance spectrometry are shown below.

$^1$H-NMR (CDCl$_3$) σ(ppm): 7.42 (d, 4H), 7.25-7.21 (m, 6H), 7.18 (t, 2H), 6.51 (d, 2H), 6.50 (d, 2H), 4.40 (m, 2H), 3.61 (s, 6H), 1.20-0.90 (s(br) 12H)

$^{13}$C-NMR (CDCl$_3$) σ(ppm): 159.39, 157.23, 139.96, 136.25, 133.90, 130.71, 130.59, 129.90, 128.19, 127.73, 126.94, 113.08, 106.41, 103.48, 70.10, 55.74, 21.65

Figure 2:
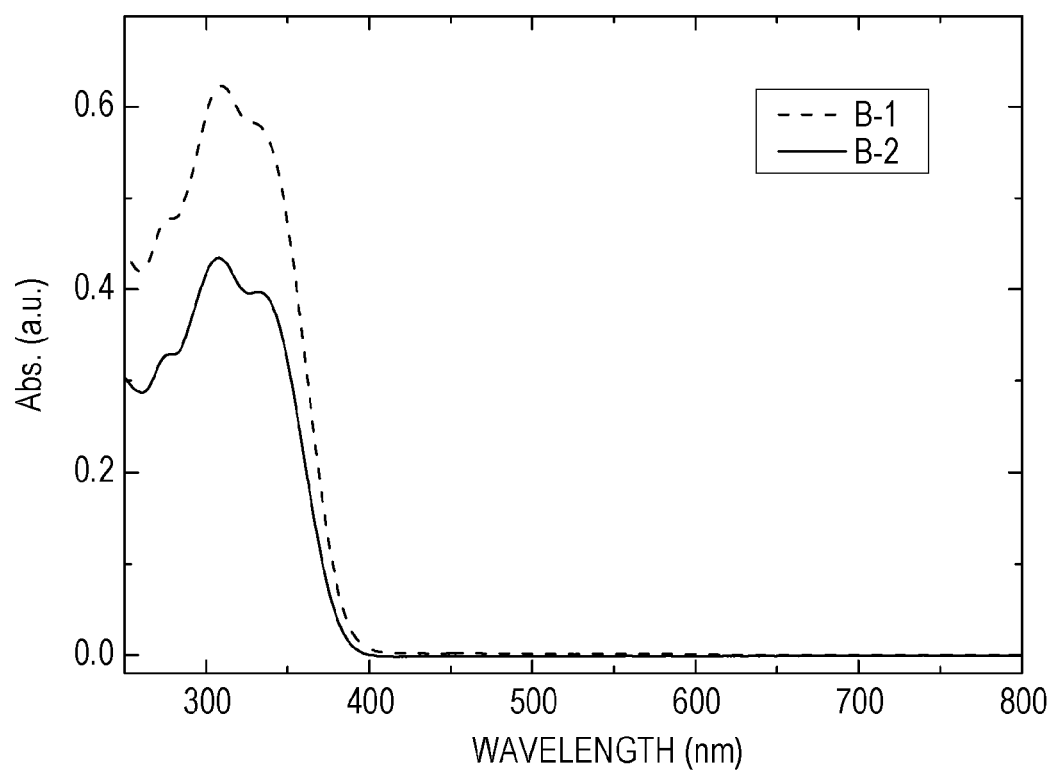
FIG. 2 shows ultraviolet-visible absorption spectra of exemplary compounds B-1 and B-2 in a neutral state.

The exemplary compound B-2 thus obtained was dissolved in chloroform, and the absorption spectrum of this solution measured by using an ultraviolet-visible spectrophotometer (V-560 manufactured by JASCO Corporation) is shown in FIG. 2.

λ max at which the absorption peak showed the maximum intensity was 307.5 nm in the ultraviolet region. Since having no absorption over the entire visible light region, the exemplary compound B-2 was found as a transparent material.

Example 2

Synthesis of Exemplary Compound B-1

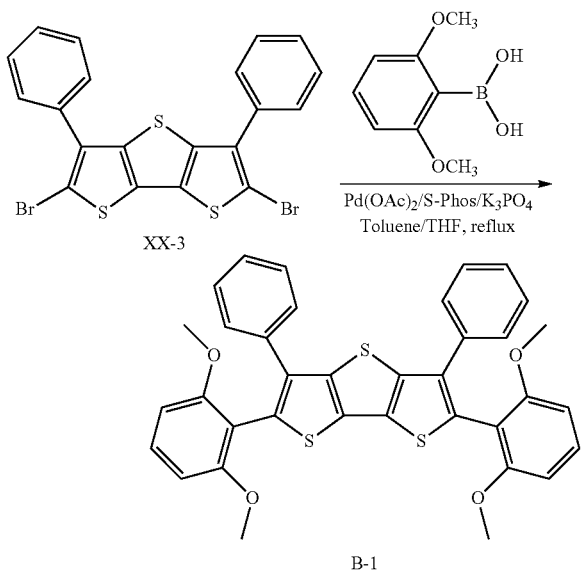

B-1

In a 50-ml reaction container, 300 mg (0.593 mmol) of XX-3 obtained in Example 1, 431 mg (2.37 mmol) of (2,6-dimethoxyphenyl)boronic acid were mixed together in a mixed solvent of toluene and tetrahydrofuran (3 ml/3 ml), and dissolved oxygen was removed by nitrogen. Next, 2.7 mg (0.01186 mmol) of Pd(OAc)$_2$, 12.2 mg (0.02965 mmol) of 2-dicyclohexylphosphino-2',6'-dimethoxybiphenyl (S-Phos), and 682 mg (2.97 mmol) of tripotassium phosphate were added in a nitrogen atmosphere, and a reaction was performed by heat reflux for 8 hours. After a reaction solution was cooled to room temperature, concentration under reduced pressure was performed, and isolation and purification were performed by a silica gel chromatography (moving phase: hexane/chloroform=½) to give B-1 as a white solid powder (157 mg, yield: 43%).

By mass analysis (MS) and nuclear magnetic resonance (NMR) measurement, the structure of the compound B-1 was analyzed. In particular, 620 as M$^+$ of this compound was confirmed by MALDI-MS measurement. In addition, the measurement results of a nuclear magnetic resonance spectrometry are shown below.

$^1$H-NMR (CDCl$_3$) σ(ppm): 7.41 (d, 4H), 7.29-7.22 (m, 6H), 7.19 (t, 2H), 6.53 (d, 4H), 3.59 (s, 12H)

$^{13}$C-NMR (CDCl$_3$) σ(ppm): 159.03, 140.28, 136.09, 134.11, 130.75, 130.19, 130.08, 128.15, 127.66, 127.01, 112.13, 104.12, 55, 79

The exemplary compound B-1 thus obtained was dissolved in chloroform, and the absorption spectrum of this solution measured by using an ultraviolet-visible spectrophotometer as in Example 1 is shown in FIG. 2. λ max at which the absorption peak showed the maximum intensity was 309.5 nm in the ultraviolet region, and since having no absorption over the entire visible light region, the exemplary compound B-1 was found as a transparent material.

Example 3 and Comparative Example 1

Stability of Oxidation-Reduction Cycle

An oxidation-reduction cycle durability test was performed on the compound B-2 obtained in Example 1, the compound B-1 obtained in Example 2, and a compound (XX-4) used as a comparative example in which a t-butyl group having a smaller steric hindrance than that of the substituent according to the present invention was introduced into DTT (dithieno[3,2-b:2',3'-d]thiophene).

In this case, the compound of the comparative example was synthesized by a Friedel-Crafts reaction between t-butylbromide (2-bromo-2-methylpropane) and DTT. The structural formula is shown below.

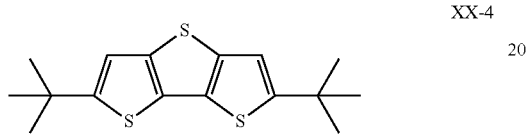

XX-4

For the durability measurement, glassy carbon was used for a working electrode, platinum was used for a counter electrode, silver was used for a reference electrode, and a dichloromethane solution was used in which tetrabutylammonium perchlorate (0.1 mol/L) as a supporting electrolyte and each of the above compounds ($1.0 \times 10^{-4}$ mol/L) were dissolved.

In this solution, a square-wave potential program including constant potential oxidation at +0.8 V (B-2 and B-1) or +1.2 V (XX-4) (vs. Ag/Ag$^+$), each of which was equal to or more than the oxidation potential of the corresponding compound, for 3 seconds and subsequent constant potential reduction at 0 V (vs. Ag/Ag$^+$) for 3 seconds was repeatedly performed 20,000 times.

The changes in oxidation peak current in cyclic voltammetry (CV) measurement before and after the oxidation-reduction cycles for 20,000 times are shown in Table.

In this table, the "rate of change in oxidation peak current" indicates a value obtained by adding the change in current from the initial current (represented by 100%) to the initial current.

TABLE

| | Rate of Change in Oxidation Peak Current after Oxidation-Reduction Cycles for 20,000 Times (%) |
|---|---|
| Example 1 (B-2) | 101 |
| Example 2 (B-1) | 98 |
| Comparative Example 1 (XX-4) | 81 |

In the compound XX-4 of Comparative Example 1, after the oxidation-reduction cycle was performed 20,000 times, the oxidation peak current was decreased, and this indicated the degradation of the compound.

On the other hand, in the compounds (B-2 and B-1) of Examples 1 and 2, even after the oxidation-reduction cycle was performed 20,000 times, the change in oxidation current was hardly observed.

The results in that the compounds according to the present invention have superior durability stability against the oxidation-reduction cycle indicates that compared to XX-4 of Comparative Example 1, the compounds B-2 and B-1 according to the present invention each have the structure to sterically protect the DTT moiety with bulky substituents each serving as the cage moiety.

In addition, it is believed that since hydrogen atoms at the 3-position and the 5-position of dithienothiophene, which probably could serve as side reaction points, were removed by the substituted phenyl groups, and since a side reaction and a degradation reaction by radical cations of DTT generated in the oxidized state were suppressed, the durability stability was enhanced.

Example 4

Measurement of Oxidation Absorption Spectrum

Confirmation of π-Dimer Formation

The absorption spectra in the oxidized state of the compound B-2 obtained in Example 1 and the compound B-1 obtained in Example 2 were measured, and whether π-dimer formation occurred or not was confirmed.

For the measurement of an oxidation absorption spectrum, platinum was used for a working electrode, platinum was used for a counter electrode, silver was used for a reference electrode, and a dichloromethane solution was used in which tetrabutylammonium perchlorate (0.1 mol/l) as a supporting electrolyte and each of the above compounds ($5.0 \times 10^{-4}$ or $1.7 \times 10^{-4}$ mol/L) were dissolved.

Figure 3:
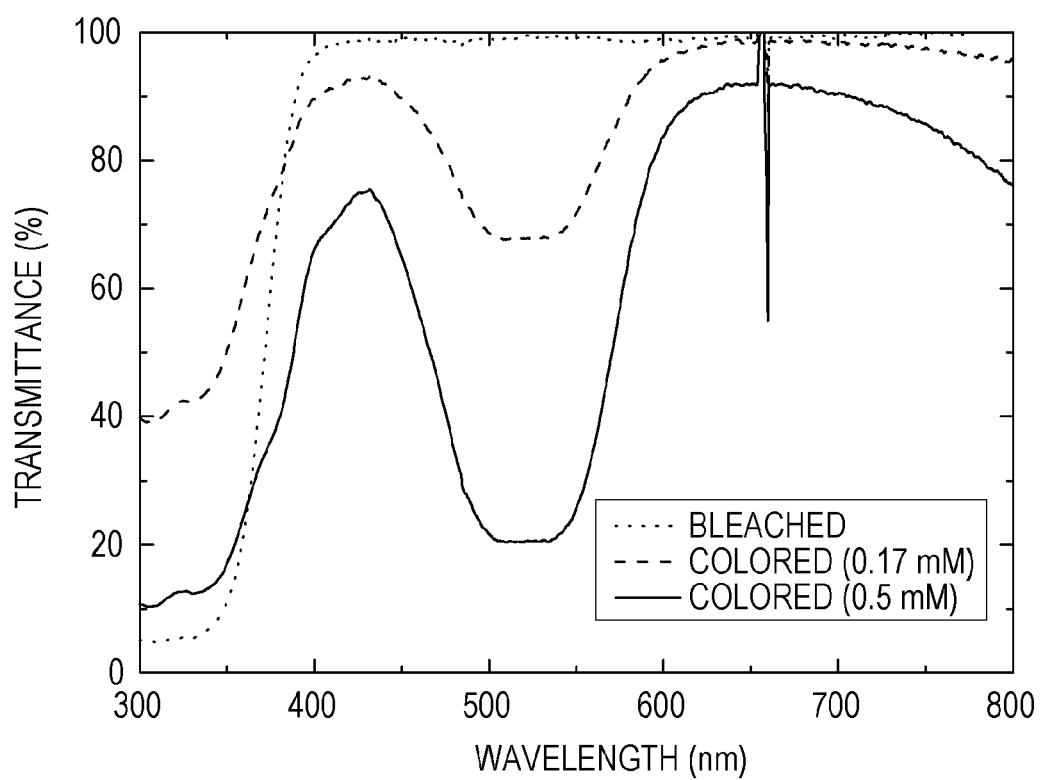
FIG. 3 shows the change in transmittance of the exemplary compound B-1 accompanied by oxidation thereof.

In this solution, constant potential oxidation at +0.9 V (vs. Ag/Ag+), which was equal to or more than the oxidation potential of the compound, was performed, and the change in transmittance was measured. The results of the compound B-1 of Example 2 are shown in FIG. 3.

In the bleached state before oxidation, absorption was not observed in the visible light region, and hence the transmittance was approximately 100% over the entire visible light region.

On the other hand, the solution was colored to purple red as oxidation progressed, the light absorption peak was observed at approximately 510 nm, and the transmittance was decreased to 20.3%.

This oxidation colored state was again returned to a colorless and transparent state by reduction, and hence electrochromic characteristics in conformity with oxidation-reduction were confirmed.

The oxidation peak described above was a single peak (unimodal distribution), and regardless of the two types of concentrations ($5.0 \times 10^{-4}$ or $1.7 \times 10^{-4}$ mol/L), the shape and the wavelength of the absorption peak were not changed.

In addition, as in the case described above, in the compound B-2 of Example 1, the change in transmittance by absorption of the single peak caused by oxidation is shown, and the shape and the wavelength of the absorption peak were not changed with the concentration.

It has been known that in the oxidized state of the compound which forms π-dimers, since the absorption wavelength of π-dimers is different from that of monomeric radical cations, the oxidation absorption peak has a bimodal distribution, and in addition, the ratio between the two peak intensities is changed in accordance with the concentration.

Hence, in the organic compound according to the present invention, it was shown that the π-dimer formation was suppressed.

Example 5

Synthesis of Exemplary Compound D-11

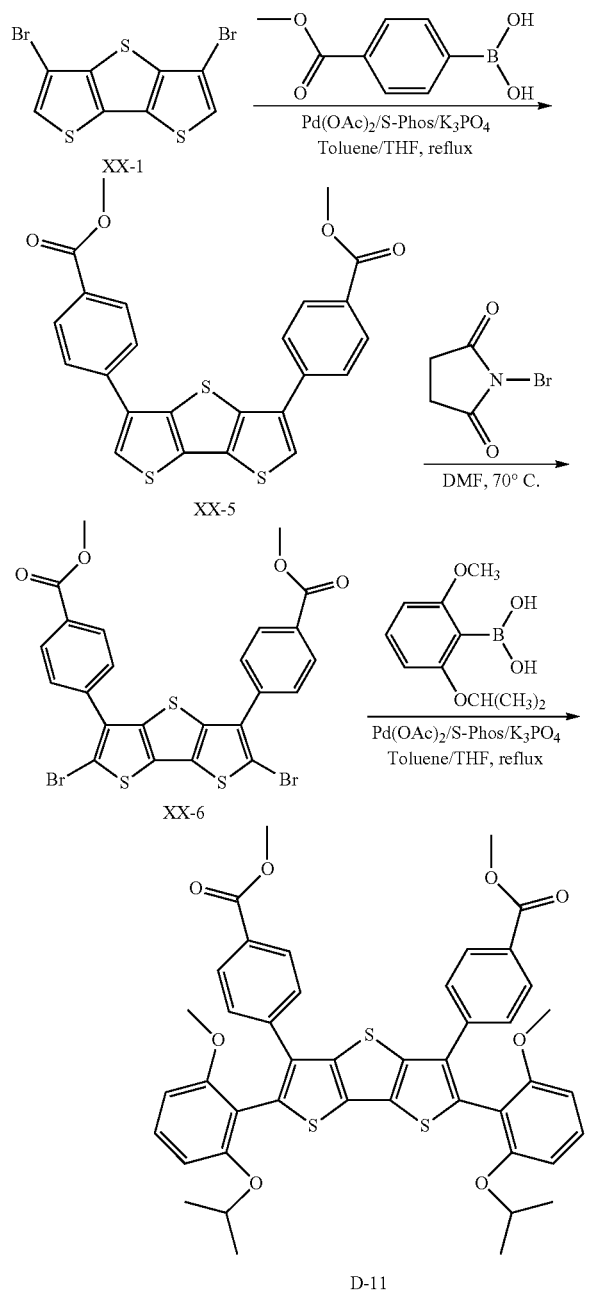

(1) In a 50-mL reaction container, 354.1 mg (1.0 mmol) of XX-1, 719.9 mg (4.0 mmol) of 4-(methoxycarbonyl)phenylboronic acid were dissolved in a mixed solvent of toluene and tetrahydrofuran (8 ml/8 ml), and dissolved oxygen was removed by nitrogen. Next, 9.0 mg (0.04 mmol) of Pd(OAc)$_2$, 41.0 mg (0.10 mmol) of 2-dicyclohexylphosphino-2',6'-dimethoxybiphenyl (S-Phos), and 1.15 g (5.0 mmol) of tripotassium phosphate were added in a nitrogen atmosphere, and a reaction was performed at 110° C. by heat reflux for 8 hours. After a reaction solution was cooled to room temperature, concentration under reduced pressure was performed, and isolation and purification were performed by a silica gel chromatography (moving phase: hexane/ethyl acetate) to give XX-5 as a white solid powder (81.5 mg, yield: 17.5%).

(2) In a 100-mL reaction container, 60 mg (0.129 mmol) of XX-5 obtained in the above (1) was dissolved in 12 ml of DMF (N,N-dimethylformamide). Next, 57 mg (0.323 mmol) of N-bromosuccinimide was added, and stirring was performed at 70° C. for 24 hours. After a reaction solution was cooled to room temperature, extraction by chloroform, water washing, and concentration under reduced pressure were performed, and as a result, a pale yellow powder XX-6 was obtained (65 mg, yield: 81%).

(3) In a 50-ml reaction container, 60 mg (0.096 mmol) of XX-6, 81 mg (0.386 mmol) of 2-isopropoxy-6-methoxyphenylboronic acid were mixed together in a mixed solvent of toluene and tetrahydrofuran (6 ml/6 ml), and dissolved oxygen was removed by nitrogen. Next, 2.2 mg (0.0096 mmol) of Pd(OAc)$_2$, 9.9 mg (0.024 mmol) of 2-dicyclohexylphosphino-2',6'-dimethoxybiphenyl (S-Phos), and 111 mg (0.482 mmol) of tripotassium phosphate were added in a nitrogen atmosphere, and a reaction was performed by heat reflux for 8 hours. After a reaction solution was cooled to room temperature, concentration under reduced pressure was performed, and isolation and purification were performed by a silica gel chromatography (moving phase: hexane/ethyl acetate) to give D-11 as a white solid powder (52 mg, yield: 68%).

By mass analysis (MS) and nuclear magnetic resonance (NMR) measurement, the structure of the compound D-11 was analyzed, and the molecular weight and the ratio of integrated values of NMR peaks well agreed with the structure. In particular, 792 as M$^+$ of this compound was confirmed by MALDI-MS measurement. In addition, the measurement results of a nuclear magnetic resonance spectrometry are shown below.

$^1$H-NMR (CDCl$_3$) δ(ppm): 7.94 (d, 4H), 7.49 (d, 4H), 7.25 (t, 2H), 6.51 (d, 2H), 6.50 (d, 2H), 4.41 (m, 2H), 3.88 (s, 6H), 3.60 (s, 6H), 1.20-0.90 (s(br), 12H)

$^{13}$C-NMR (CDCl$_3$) δ(ppm): 167.01, 159.17, 157.09, 140.92, 139.47, 132.86, 132.40, 130.99, 130.31, 129.66, 128.44, 127.60, 112.39, 106.29, 103.45, 70.15, 55.70, 52.04, 21.65

The exemplary compound D-11 thus obtained was dissolved in chloroform, and according to the measurement result obtained by using an ultraviolet-visible spectrophotometer as in Example 1, λ max at which the absorption peak showed the maximum intensity was 316.0 nm in the ultraviolet region. Since having no absorption over the entire visible light region, the exemplary compound D-11 was found as a transparent material.

In addition, as one example of the element solvent, the solubility of the compound D-11 in a propylene carbonate solution of LiCO$_4$ (supporting electrolyte, 0.1 mol/L) was confirmed. According to the result, it was confirmed that this compound was dissolved at a concentration of 9 mmol/L and that the solubility thereof was higher than the solubility (6 mmol/L) of the compound B-2 of Example 1. The reason for this is believed that since having an ester group-containing phenyl group at the 3-position of DTT, the compound D-11 has an improved solubility into propylene carbonate, which is a polar solvent.

<Measurement of Oxidation Absorption Spectrum>

The measurement of the oxidation absorption spectrum of the obtained compound D-11 was performed as in Example 4 using a dichloromethane solution in which tetrabutylammonium perchlorate (0.1 mol/L) and D-11 ($5.0 \times 10^{-4}$ mol/L) were dissolved. The solution of D-11 was colored to purple red as oxidation progressed, the light absorption peak was observed at 541.5 nm, and the transmittance was decreased to 36.3%. This oxidation colored state was again returned to a colorless and transparent state by reduction, and the electrochromic characteristics in conformity with oxidation-reduction were confirmed. In addition, since the shape and the absorption wavelength of this oxidation absorption peak were not changed with the concentration, it was shown that as in Example 4, the formation of π-dimers was suppressed.

The reason the organic compound according to the present invention is excellent in suppressing the formation of π-dimers is believed that since increasing the intermolecular distance between radical cations generated in the oxidized state, the ortho-position substituted phenyl groups each serving as the cage moiety suppress the intermolecular interaction.

When the EC element is used as a device required to have monochromaticity, the suppression of the formation of π-dimers has a significant effect to obtain the monochromaticity of the absorption spectrum.

As described above, the organic compound according to the present invention is a material that is transparent in the neutral state, has high durability against oxidation-reduction repetition, and is excellent in suppressing the formation of π-dimers.

When the organic compound according to the present invention is used for an EC element, there is provided an EC element that has no light absorption in the visible light region in the bleached state and high transparency, is excellent in durability, and is also excellent in color characteristic stability in the colored state against the change in temperature.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-011300 filed Jan. 23, 2012, which is hereby incorporated by reference herein in its entirety.

What is claimed is:

1. An organic compound represented by the following general formula [1]

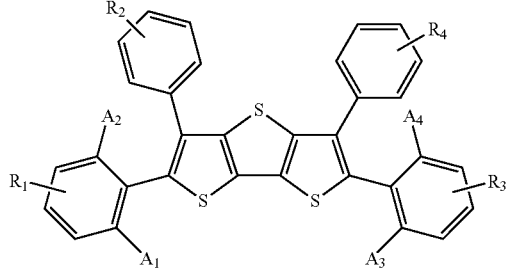

wherein in the general formula [1], $A_1$ to $A_4$ are each independently selected from the group consisting of a hydrogen atom, an alkyl group having 1 to 20 carbon atoms, an alkoxy group having 1 to 20 carbon atoms, and an aryl group, and at least one of $A_1$ to $A_4$ represents the alkyl group, the alkoxy group, or the aryl group, the aryl group may have an alkyl group having 1 to 4 carbon atoms or an alkoxy group having 1 to 4 carbon atoms as a substituent, $R_1$ to $R_4$ each independently represent a hydrogen atom, a halogen atom, an alkyl group having 1 to 20 carbon atoms, an alkoxy group having 1 to 20 carbon atoms, an alkyl ester group having 1 to 20 carbon atoms, an aryl group, or a cyano group, and the aryl group may have an alkyl group having 1 to 4 carbon atoms as a substituent.

2. The organic compound according to claim 1, wherein at least one of $A_1$ to $A_4$ represents an alkoxy group having 1 to 20 carbon atoms.

3. The organic compound according to claim 2, wherein the least one of $A_1$ to $A_4$ represents a methoxy group or an isopropoxy group.

* * * * *